United States Patent [19]
Riek et al.

[11] Patent Number: 5,788,709
[45] Date of Patent: Aug. 4, 1998

[54] DEVICE FOR REMOVAL OF TISSUE OR SUCH FROM THE ABDOMINAL CAVITY

[76] Inventors: Siegfried Riek, Konrad-Witz-Strasse 11, 78628 Rottweil; Karl-Heinz Bachmann, Fronwiesen 9; Thomas Gaiselmann, Teichwiesen 4, both of 78667 Villingendorf, all of Germany

[21] Appl. No.: 494,023

[22] Filed: Jun. 23, 1995

[30] Foreign Application Priority Data

Apr. 26, 1995 [DE] Germany .................. 195 15 280.8

[51] Int. Cl.$^6$ .................. A61B 17/42; A61B 17/46
[52] U.S. Cl. .................. 606/114; 606/110; 606/127; 606/128
[58] Field of Search .................. 606/114, 113, 606/110, 185, 1, 108, 127, 128; 604/164, 165; 128/749

[56] References Cited

U.S. PATENT DOCUMENTS

| | | | |
|---|---|---|---|
| 4,905,691 | 3/1990 | Rydell | 606/47 |
| 5,037,379 | 8/1991 | Clayman et al. | 600/37 |
| 5,037,397 | 8/1991 | Clayman et al. | |
| 5,176,688 | 1/1993 | Narayan et al. | 606/185 |
| 5,190,542 | 3/1993 | Nakao et al. | 606/47 |
| 5,192,264 | 3/1993 | Pleatman | 606/114 |
| 5,337,754 | 8/1994 | Heaven et al. | 606/114 |
| 5,341,815 | 8/1994 | Cofone et al. | 128/749 |
| 5,368,545 | 11/1994 | Schaller et al. | 600/37 |
| 5,391,156 | 2/1995 | Hildwein et al. | 606/185 |
| 5,397,320 | 3/1995 | Essig et al. | 606/110 |
| 5,460,170 | 10/1995 | Hammerslag | 606/198 |
| 5,480,404 | 1/1996 | Kammerer et al. | 606/113 |
| 5,611,803 | 3/1997 | Heaven et al. | 606/114 |
| 5,630,822 | 5/1997 | Hermann et al. | 606/114 |

FOREIGN PATENT DOCUMENTS

| | | | |
|---|---|---|---|
| 537533 | 4/1993 | European Pat. Off. | 606/113 |
| A-0 5a42 103 | 5/1993 | European Pat. Off. | |

*Primary Examiner*—Robert A. Hafer
*Assistant Examiner*—Justine R. Yu
*Attorney, Agent, or Firm*—Gary M. Nath; Irvin A. Lavine; Nath & Associates

[57] ABSTRACT

A flexible bag is introduced into the abdominal cavity to remove larger portions of tissue from the abdominal cavity through a threaded casing introduced into the abdominal wall. The bag features a side opening through which the tissue can be moved into the bag. The end opening of the bag remains extracorporeal to the threaded casing. After pulling out the bag the side opening is located outside of the threaded casing and the tissue is tightly enclosed by the portion of the bag remaining in the abdominal cavity and is accessible for cutting up the tissue form outside, through the threaded casing.

16 Claims, 9 Drawing Sheets

DEVICE FOR REMOVAL OF TISSUE OR SUCH FROM THE ABDOMINAL CAVITY

BACKGROUND OF THE INVENTION

1. Field of the Invention

The invention pertains to a device for removal of tissue or such from the abdominal cavity.

2. Description of the Related Art

In minimal invasive surgery the operative access to the abdominal cavity takes place through trocar casings installed through an abdominal wall. The advantage of minimal invasive surgery is that there is a small surgical wound and the resultant reduced surgical pain, shorter recovery times and unobtrusive surgical scars. The advances in surgical techniques with minimal invasive surgery also makes possible the surgical removal of larger portions of tissue, e.g. of cysts, tumors or even organs or parts of organs, such as the uterus, the kidney or portions of the intestine. If such tissue portions, organs, etc., called generically "tissue" in the application as set forth below are removed surgically from the abdominal cavity, then the problem remains that this tissue frequently has a larger diameter than the trocar casing. Thus, the tissue cannot be removed from the abdominal cavity through this trocar casing.

One possibility for elimination of this problem includes cutting up the tissue in the abdominal cavity. This method has severe disadvantages. When tumors are cut up, there is a danger that malignant cells will move into the abdominal cavity. During the removal of cysts, their content may spill into the free abdominal cavity, which can lead to inflammation and possibility also to the transfer of malignant cells. In addition, cutting up tissue in the abdominal cavity under the conditions of minimal invasive surgery is technically complicated and very time consuming. In certain methods (with motor-driven morcellators) there is a high danger of injury for the organs and blood vessels in the abdominal cavity.

In order to counter these disadvantages, a device using a flexible bag is introduced into the abdominal cavity through the trocar casing. The bag is introduced fully into the abdominal cavity and is held in position be means of filaments. In the interior of the abdominal cavity, the tissue is moved into the bag through the end opening, whereupon the end opening is pulled together and closed by means of filaments run to the outside through the trocar casing. However, the bag with the enclosed tissue cannot be pulled through the trocar casing when the enclosed tissue cannot be pulled through the trocar casing when the diameter of the tissue is too large. The existing skin incision for the trocar casing therefore has to be expanded in order to remove the bag with the tissue in the abdominal cavity. The advantages of the minimal invasive surgical technique are thus mostly lost.

The conventional art has provided no suggestion for quickly and efficiently removing tissue pieces that are substantially larger than a mandrin inserted to obtain access to that tissue. The conventional art appears to be limited to relatively slow and cumbersome methods of reducing and removing large tissue samples from within the human body.

SUMMARY OF THE INVENTION

Accordingly, it is one object of the present invention to provide apparatus to quickly remove tissue samples from a human body with minimum invasive measures.

It is another object of the present invention to provide apparatus to effect greater ease in the removal of tissue samples from the human body.

It is still an additional object of the present invention to provide apparatus to speed operative procedures involving the removal of tissue from within the human body.

It is yet a further object of the present invention to provide apparatus to more easily reduce human tissue within a human body for removal of that tissue.

These and other objects of the present invention are achieved by a device for removing tissue from a cavity in the human body through the use of a threaded casing inserted into the flesh surrounding the cavity. The device includes a flexible bag which is arranged to be inserted through the threaded casing into the cavity in the human body. The bag has an end opening that is arranged to remain outside the human body. A second opening in the side of the bag is arranged to open when the bag has been inserted into the human body so that tissue can be brought into the bag through the second opening. The second opening is configured so that once the tissue has entered the bag through the second opening, the tissue drops into a bottom portion of the bag beneath the side opening so that the bag, which is collapsible from the bottom portion to the end opening, can be pulled through the threaded casing and the portion of the bag including the side opening moved to the exterior of the human body. At least one cutting filament is arranged at the bottom portion of the bag with two ends of the cutting filament placed at the first opening of the bag. When one end of the filament is pulled, the filament is moved upwards from the bottom of the bag, cutting through tissue located at the bottom of the bag. Thus, the tissue is reduced in size for easy removal.

DESCRIPTION OF THE PREFERRED EMBODIMENTS

The present invention is directed to a bag for the removal of tissue; in addition to this end opening, the bag also has a side opening in the wall region between the end opening and the base of the bag. The bag is introduced into the abdominal cavity through a threaded casing, but in such a manner that it does not go entirely into the abdominal cavity, but rather its end opening remains outside the threaded casing and the human body. The tissue can be moved into the bag in the abdominal cavity through the side opening which is located within the abdominal cavity when the bag is introduced therein. Next, the bag is pulled out through the threaded casing until the side opening is located extracorporeally outside of the threaded case. Thus, the tissue is fully enclosed in the abdominal cavity in an uptake volume at the base of the bag, whereby the interior of the bag now has access only to space outside the body.

If the diameter of the tissue is smaller than the inside diameter of the threaded casing, then the bag with the enclosed tissue can be pulled out completely through the threaded casing. However, if the tissue enclosed in the bag has a larger diameter than the inside diameter of the threaded casing, then the tissue is cut up in the bag since the inside space of the bag is externally accessible by means of its end opening, through the threaded casing. The uptake volume of the bag holding the tissue is located within the abdomen and is fully enclosed so that there is no danger that tissue fragments, malignant cells, cyst content or similar material can get into the free abdominal cavity when cutting up the tissue.

The intra-abdominal cutting up of the tissue in the bag can occur from the outside using suitable instruments, such as microforceps, micropunches, microshears or cylinder punches which are inserted from the open end of the bag and through the threaded casing. Cylinder punches can preferably have a continuous diameter adjustment and thus they can be readily adapted to the situation and to the different diameters of the threaded casing. For better removal of the tissue, of the interior wall of the threaded casing can be shaped or coated so that tissue can slide in only one direction.

If the tissue is a cyst, it can be punctured externally through the open end of the bag and suctioned out. When dealing with soft, easily cuttable tissue, then preferably, cutting devices can be placed in the bag that are externally operable to transect the tissue in the bag. Cutting devices of this type are preferably cutting or sawing filaments that surround the tissue located in the bag and can be pulled out from the outside in order to cut through and cut up the tissue.

In order to simplify the cutting and dissecting of the tissue, in the region of the uptake volume of the bags in its interior, mounting features are provided that securely hold the tissue in the bag so that it cannot escape from the cutting tools. The mounting features are preferably positioning pins in the region of the base of the bag that penetrate into the tissue and keep it in a fixed position. Alternatively or, in addition, for fixing the tissue in place, the inner wall surface of the bag can also be made rough. The bag can also be double-walled to optimize dependability; it can have two overlapped walls which can contain tissue inlays (thin wire mesh, plastic mesh, cloth mesh) for reinforcement. In addition, spacers of solid, liquid or gaseous materials can be installed between the doubled bag walls.

Figure 1:
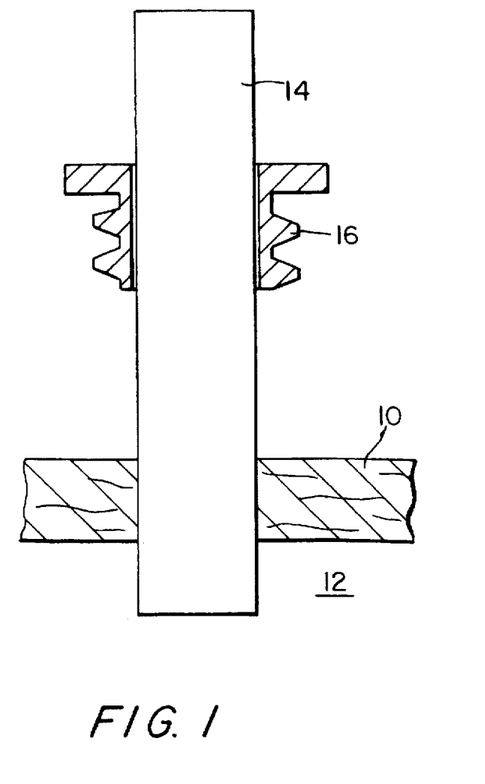
FIG. 1 is a sectional view of apparatus forming part of the present invention.

FIG. 1 shows schematically the abdominal wall 10 which seals off the abdominal cavity 12. The abdominal wall 10 is perforated by means of a trocar. By using a mandrin 14 which is employed in place of conventional trocar, the abdominal wall 10 is kept open. A threaded casing 16 provided with an external thread is seated on the mandrin 14.

Figure 2:
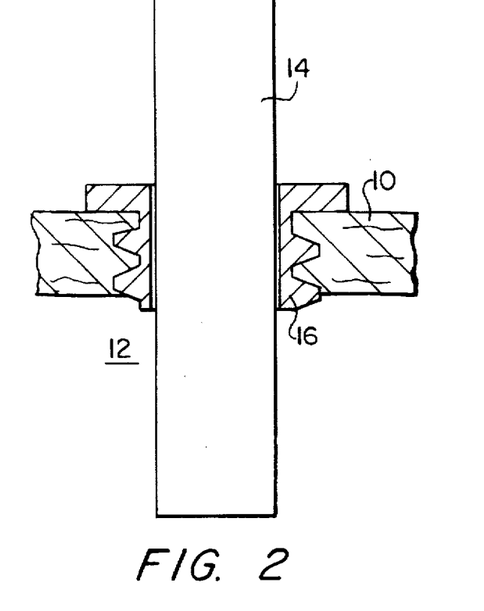
FIG. 2 is a sectional view showing the attachment of a casing to the skin of a patient.

As FIG. 2 shows, the threaded casing 16 is installed in the perforation hole of the abdominal wall 10 and is fixed in place in the abdominal wall 10 by means of its outer thread.

Figure 3:
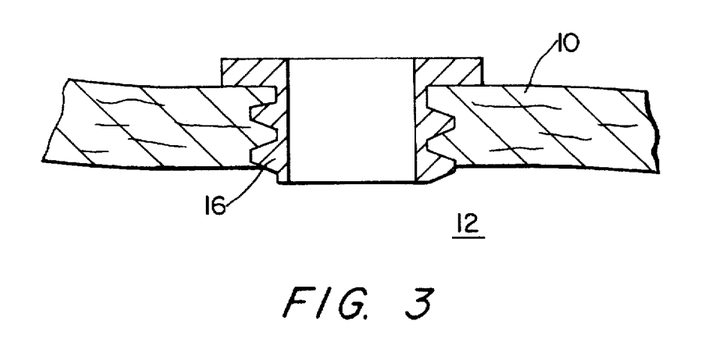
FIG. 3 is a sectional view showing the casing after withdrawal of the trocar of FIG. 2.

As FIG. 3 shows, the mandrin 14 is now removed so that the abdominal cavity 12 is accessible by means of the threaded casing 16. If necessary, the threaded casing 16 can be provided with a valve in a known manner.

Figure 4:
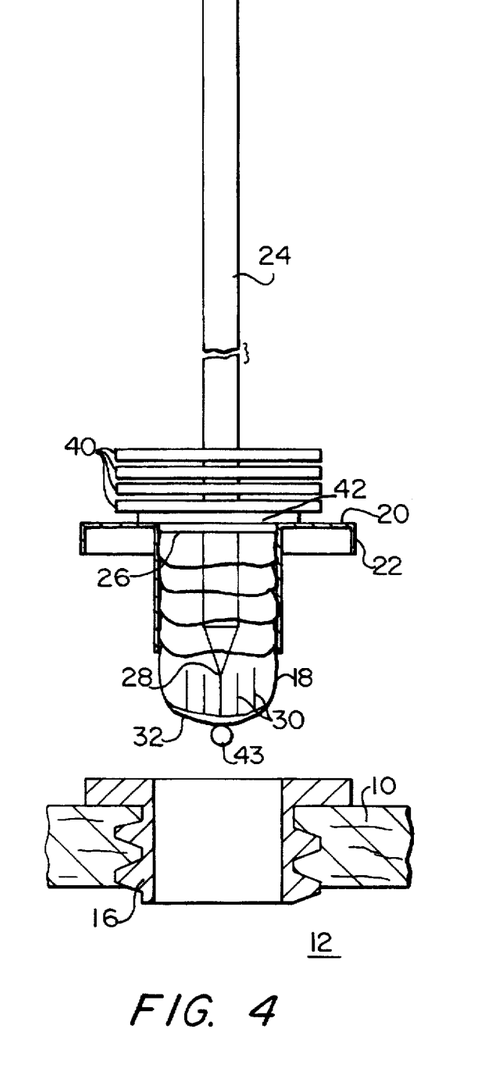
FIG. 4 is an exploded partly in section showing a bag and apparatus for inserting the bag of the present invention into a human body.

FIG. 4 shows a bag 18 made of a flexible, tear-resistant and elastic plastic that is preferably made of optically transparent material and is folded together for insertion into an insertion and safety casing 20. The axial length of the insertion and safety casing 20 can correspond to the axial length of the threaded casing 16. The insertion and safety casing 20 can be an adapter sleeve open on one side.

Figure 5:
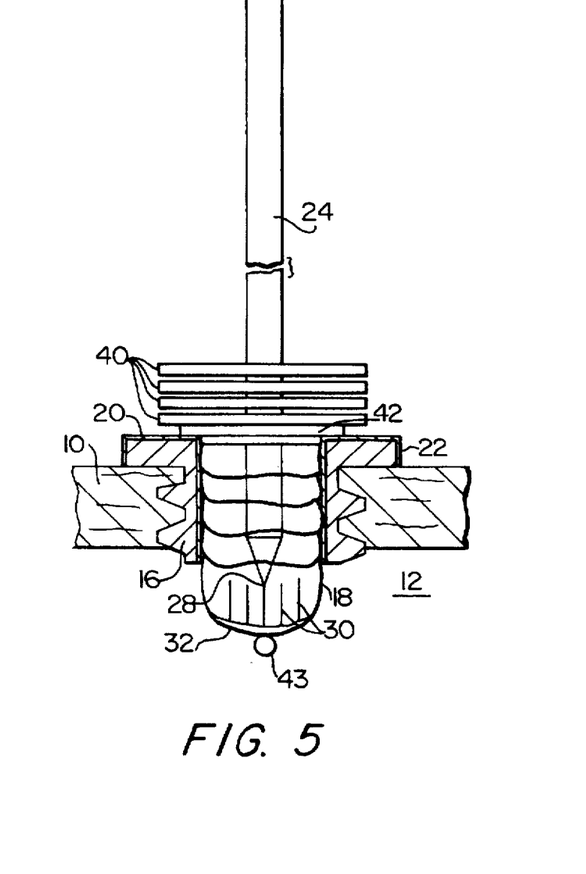
FIG. 5 is a partly sectional of the bag partly inserted through the casing.

As FIG. 5 shows, the insertion and safety casing 20 is inserted into the threaded casing 16 and its end flange 22, which makes a gas-tight seal, is supported outside the body against the threaded casing 16. The bag 18 is open outside the body where its end opening 26 is detachably connected to a sealing element 42 of the insertion and safety casing 20.

Figure 6:
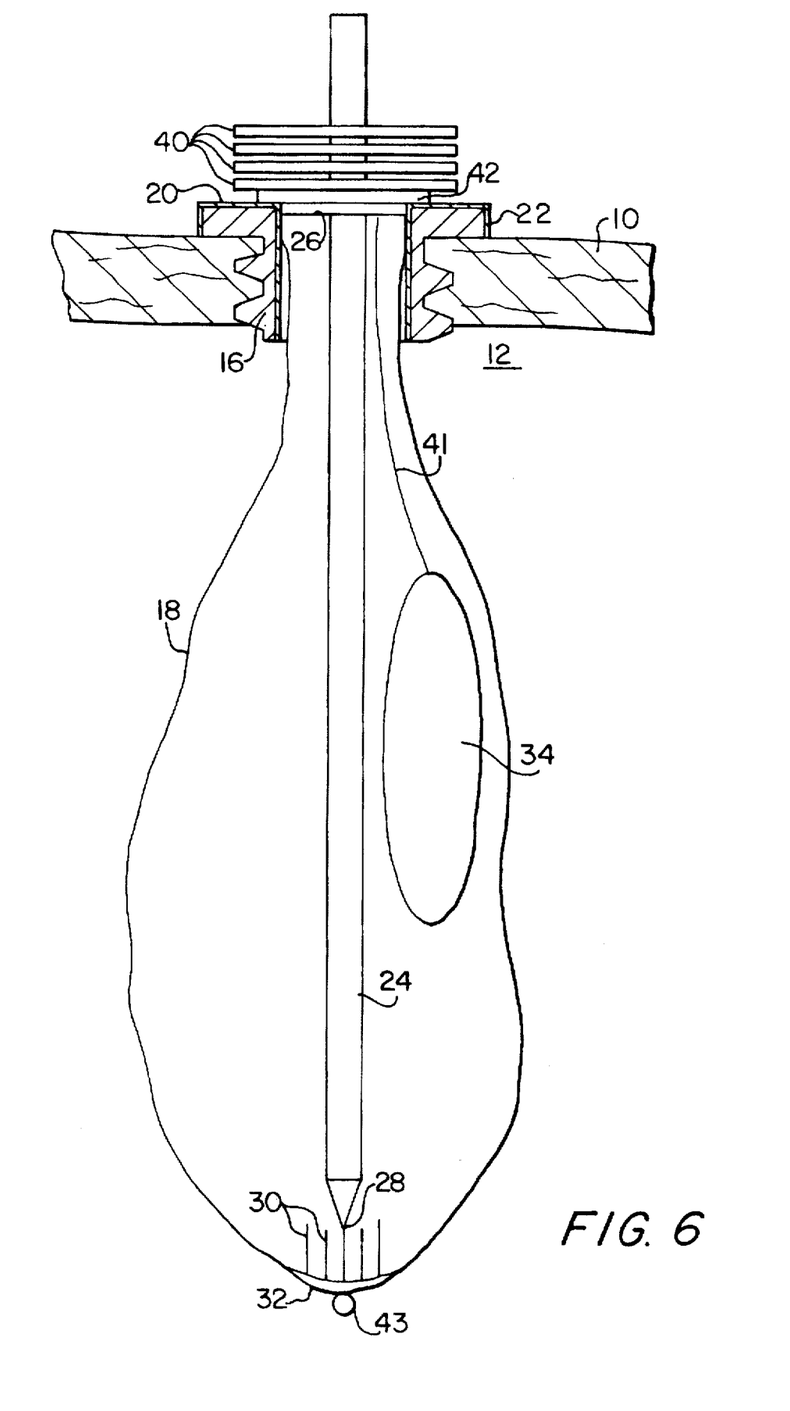
FIG. 6 is a partly sectional view showing the bag of the present invention within a cavity in a human body.

After insertion of the insertion and safety casing 20 into the threaded casing 16, the bag 18 is introduced into the abdominal cavity 12, as FIG. 6 shows. In this case, an insertion tool 24 can be used that extends into the bag 18 through to the end opening 26 of the bag 18 and is fastened by a predetermined breaking point 28 to a central positioning pin 30 of the strengthened base of the bag 32. By of coaxial insertion of the tool 24, the bag 18 deployed in the abdominal cavity 12. Alternatively, the bag can be deployed within the abdominal cavity by a manipulation loop 43. At the side of the wall of the bag 18, there is a side opening 34 that is located in the abdominal cavity 12 and deployed. An expanding ring with shape memory keeps the side opening 34 open when the bag 18 is deployed in the abdominal cavity 12. A precise placement of the side opening 34 in the abdominal cavity 12 is possible with the mandrin 24 or the manipulation loop 43.

Figure 7:
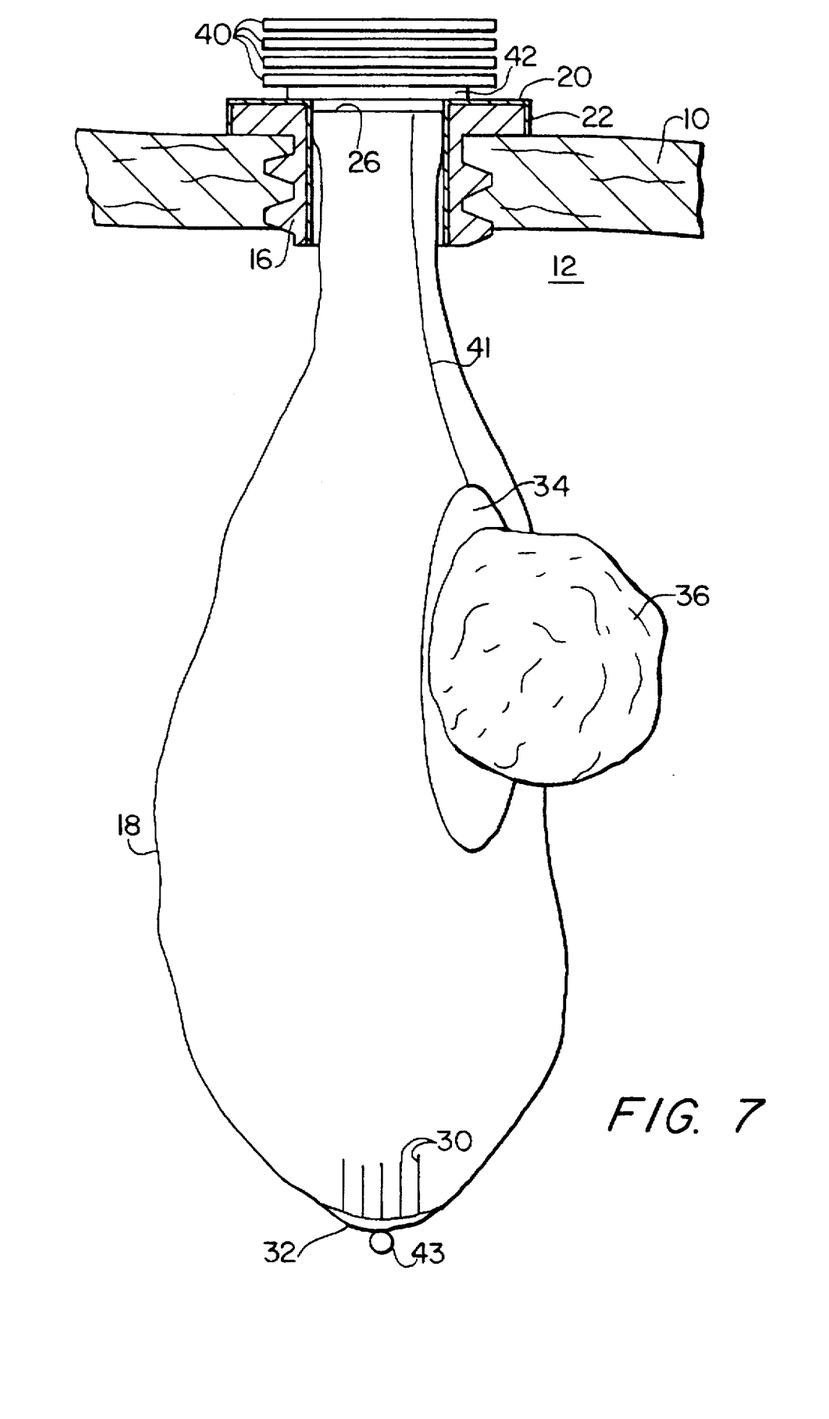
FIG. 7 is a partly sectional view showing the introduction of tissue into the bag.

After insertion of the bag 18, the mandrin 24 is twisted off at the predetermined breaking point 28 and pulled out of the bag 18. As FIG. 7 shows, any surgically separated tissue 36 in the abdominal cavity 12 can now be moved through the side opening 34 into the bag 18.

Figure 8:
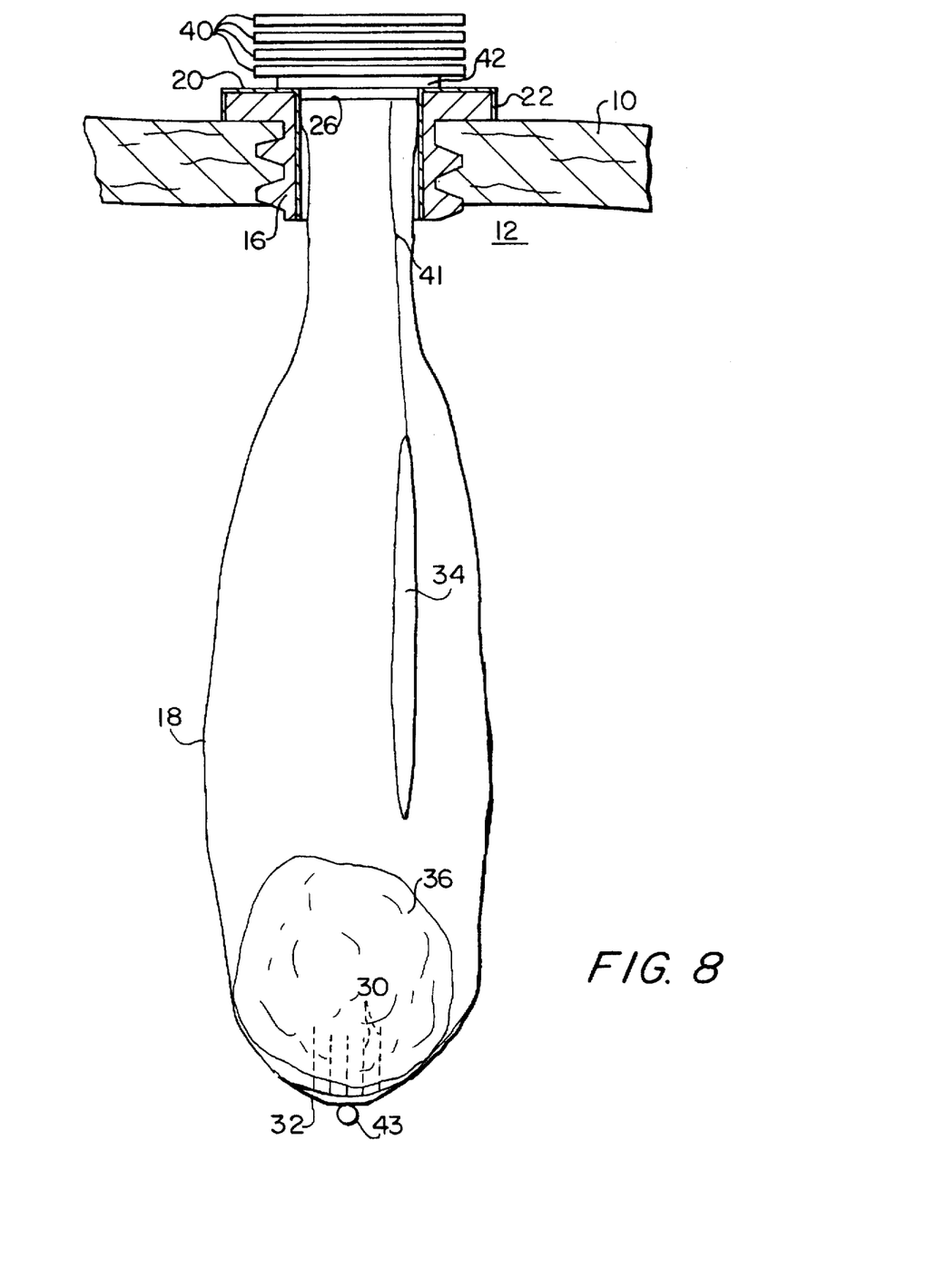
FIG. 8 is a partly sectional view showing the storage of human tissue at the bottom of the bag.

As FIG. 8 shows, the tissue 36 moves into an uptake volume in the bottom of the bag 18 that is between the base of the bag 32 and the side opening 34. Now the tissue 36 is seated on the positioning pins 30 that are installed in the reinforced base 32 of the bag 18 or are formed onto said base and whose points extend into the interior of the bag 18. These positioning pins 30 are constructed so that they cannot cause any injury to the bag 18.

Figure 9:
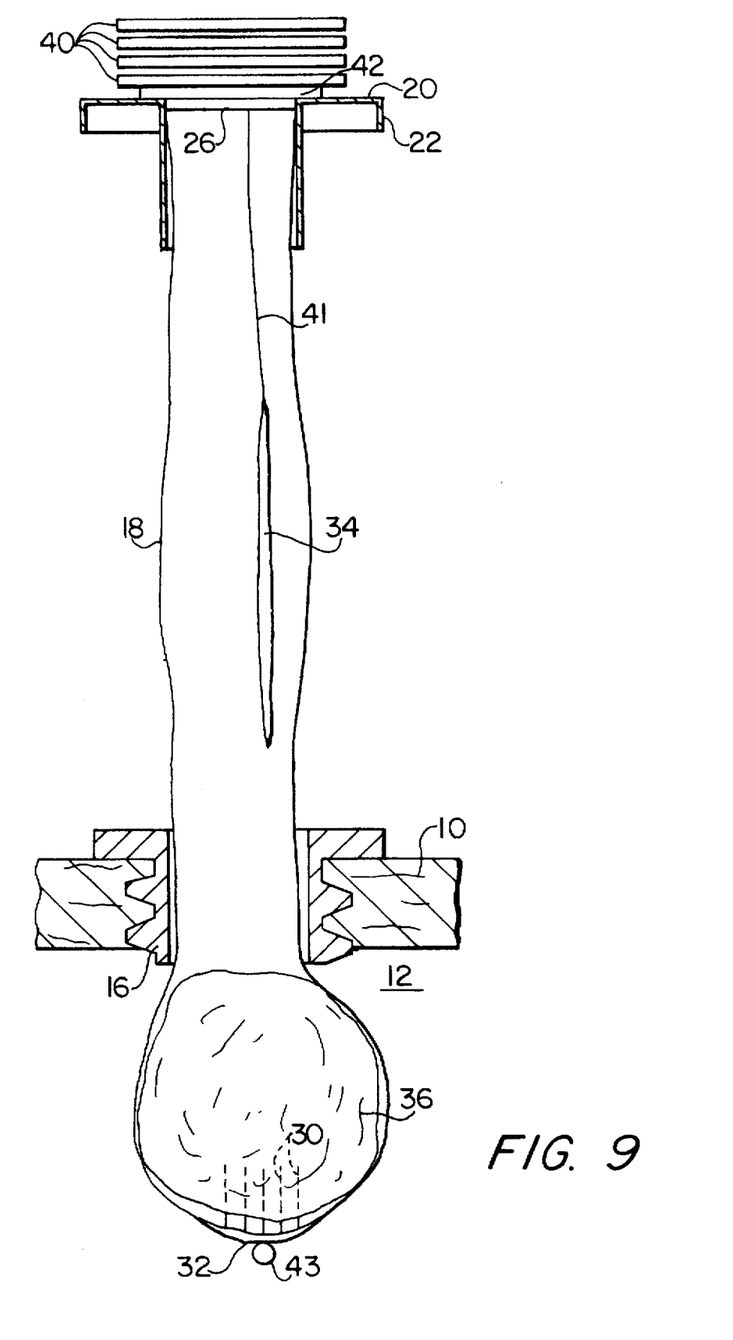
FIG. 9 is a partly sectional view showing the bag partly withdrawn from the cavity of the human body.

As FIG. 9 shows, the insertion and safety casing 20 is pulled upwardly and the bag 18 are subsequently is thereby partially withdrawn from abdominal cavity 12, collapsing from adjacent end opening 26 to adjacent the base of the bag 18 as it passes through casing 16".

If the diameter of the tissue 36 is less than the inside diameter of the threaded casing 16, then the bag 18 with the enclosed tissue 36 can be pulled out entirely so that the tissue is thereby removed from the abdominal cavity.

However, if the tissue 36 has a greater diameter than the inside diameter of the threaded casing 16, as illustrated in FIG. 9, then the bag 18 can only be pulled out until the tissue 36 within the bag 18 causes the outwardly bulging part of the bag 18 to come into contact with the intra-abdominal end of the threaded casing 16, as shown in FIG. 9. Thus, the intra-abdominal space is sealed gas-tight. The side opening 34 is located at a distance from the base 32 of the bag 18 such that the side opening 34 is already entirely pulled past the threaded casing 16 and is located outside of the threaded casing 16 when the bulge in bag 18, caused by enclosed tissue 36, comes to rest against the threaded casing 16. Thus, the tissue 36 is sealed tight within the abdominal cavity 12 due to the bag 18.

If the tissue 36 comes to rest against the threaded casing 16 when pulling out the bag 18, the tensile force applied to the bag 18 causes the positioning pin 30 of the base of the bag 32 to press into the tissue 36. The tissue 36 is thus fixed between the positioning pin 30 and the threaded casing 16 to prevent rotation and lateral movement. In addition, due to its elastic design, the bag 18 can compress the enclosed tissue 36 and this is reinforced by the prevailing intra-abdominal pressure (after $CO_2$ insufflation of the pneumoperitoneum).

Figures 10, 10A:
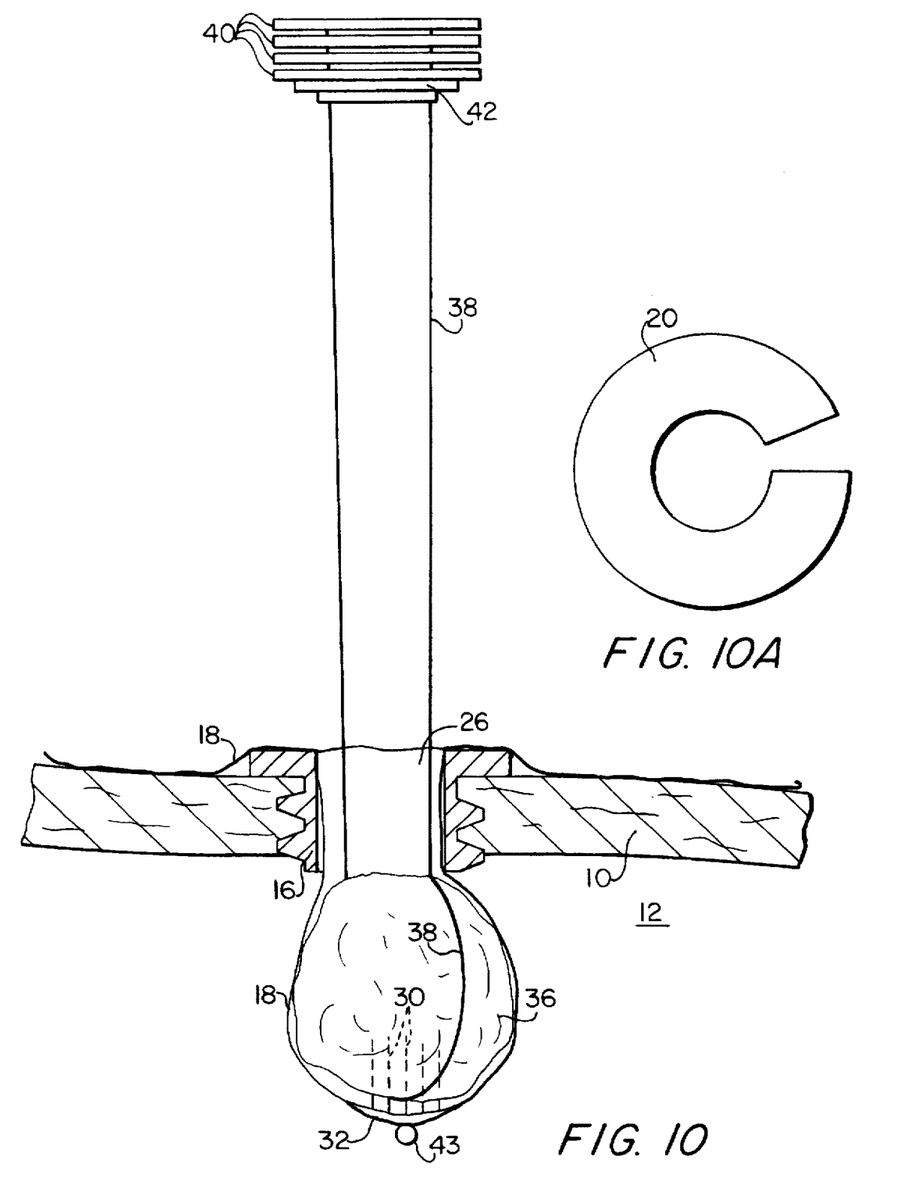
FIG. 10 is a partly sectional view showing a single cutting filament.
FIG. 10A is a plan view of an insertion and safety casing forming part of the present invention.

The bag 18 can now be separated at its open end 26 from the sealing element 42, unfolded along the fracture lines 41 and spread out over the threaded casing 16, as shown in FIG. 10. In this position, the bag 18 is secured in place preferably to the threaded casing 16 due to insertion of the insertion and safety casing 20 (in threaded casing 16), which presses the bag 18 against the inside wall of the threaded casing 16, due to its construction as a clamping sleeve open on one side (see FIG. 10A), and which has on its flange 22 a clamping mechanism to fix the bag 18 in place. Thus, the bag 18 is secured against sliding into the abdominal cavity and the tissue 36 is held in fixed position. The insertion and safety casing 20 can also be formed by two casings, an insertion casing and a safety casing.

For example, if the tissue 36 is a cyst, then it can be punctured under direct view through the insertion and safety casing 20 and the end opening of the sack 18 and suctioned. After suctioning and emptying the cyst, it can be pulled out and removed together with the bag through the threaded casing 16.

Other tissue 36 can be cut by means of suitable instruments, e.g. forcepts, punches ro shears that are introduced from the outside while being viewed, through the insertion and safety casing 20 into the bag 18, in order to cut up the tissue 36 held against the inner end of the threaded casing 16. The cut up pieces of tissue can be pulled out be means of a gasping instruments or suctioned, or removed with a hollow cylinder punch. The cutting up process can be tracked extracorporeally, and, by means of a laparoscope lens (from an existing, second incision), intra-abdominally.

In the case of the easily cuttable tissue 36, e.g. tumors, organs or parts of organs, preferably cutting elements are present in the bag 18, as is shown in the sample design of the figure. The cutting elements can be introduced through the insertion and safety casing 20 after initial use of the cutting elements, they may be employed for additional cutting up of the tissue.

These cutting features consist, in the illustrated embodiment, of cutting filaments 38 that are shown the form of a loop in the bag 18. The loops of cutting filaments 38 in this case are installed mostly in an axial plane in the bag 18 and are releasable mounted to the inside wall of the bag 18 by suitable means. The cutting filaments 38 run along the base of the bag 32 between the positioning pins 30 and are releasable mounted to the base 32 of the bag 18. Due to the placement of cutting filaments 38 between the positioning pins 30, slippage of the cutting filaments 38 from the tissue 36 is impossible and the cutting direction is established. The axial plane of the loops of the individual cutting filaments 38 in this case are offset to each other at an angle. For example, four loops offset by 45° to each other are provided. The free ends of the loops of the cutting filaments 38 are run out through the end of the opening 26 of the bag 18 and are attached to one of the extractor ring 40. The extractor rings 40 of the individual cutting filaments 38 are seated axially on each other, and are supported by the sealing element 42. Since the loops of the cutting filaments 38 intersect at the base of the bag 32, the extractor rings 40 are situated so that the cutting filament 38, and this cutting filament is the top one at the point of intersection of the cutting filaments 38 is attached to the uppermost of the extractor rings 40 the other cutting filaments 38 are in sequence attached to the other extractor rings.

Due to the arrangement and mounting of the cutting filaments 38 to the inside wall of the bag 18, the tissue 36 necessarily moves into the loops when it is moved through the side opening 34 into the bag 18. The loops of the cutting filaments 38 surround the tissue 36 in cutting planes which are axially offset to each other, as shown in FIG. 10.

Figure 11:
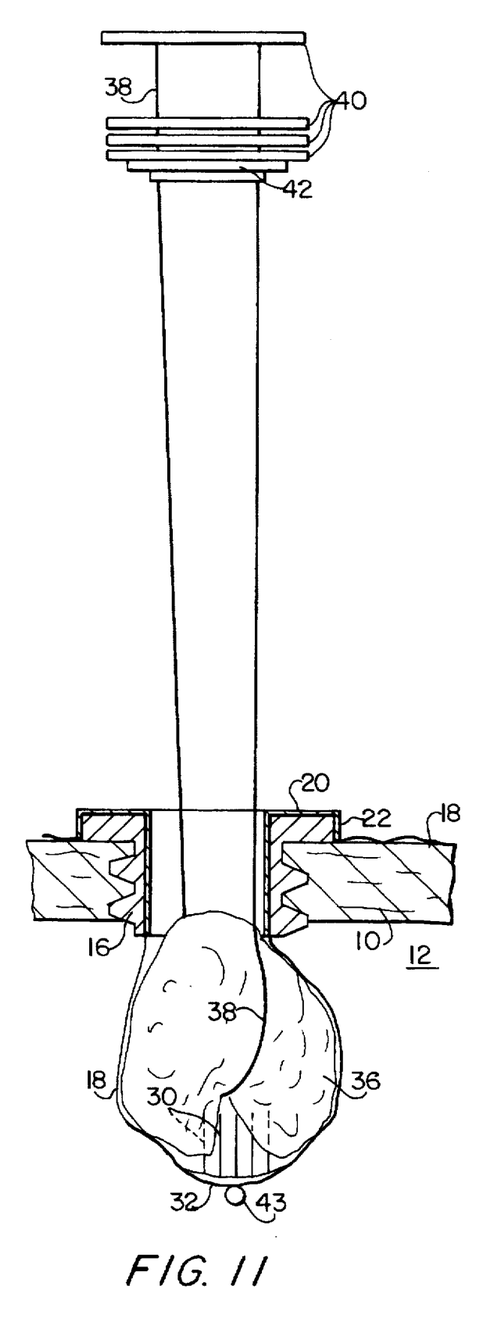
FIG. 11 is a party sectional view showing the cutting of a specimen by the cutting filament.
Figure 13:
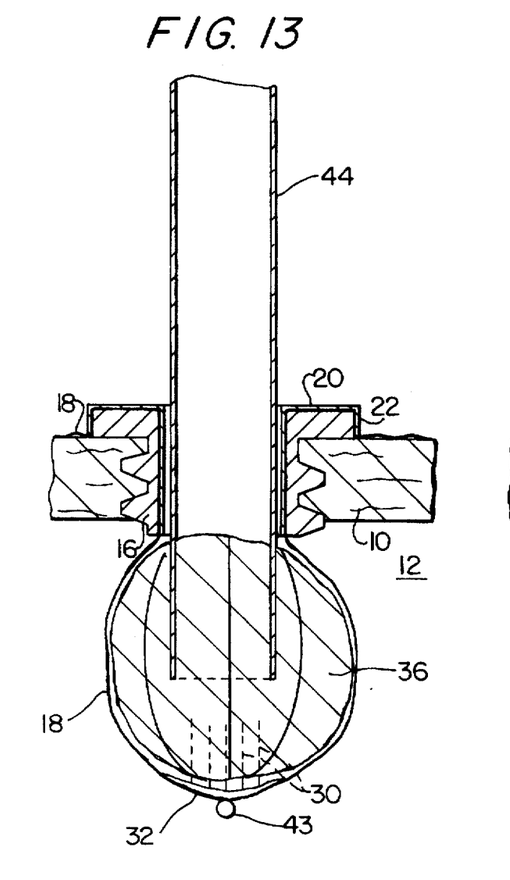
FIG. 13 is a partly sectional view showing a hollow punch for dissecting human tissue in the bag.
Figure 13A:
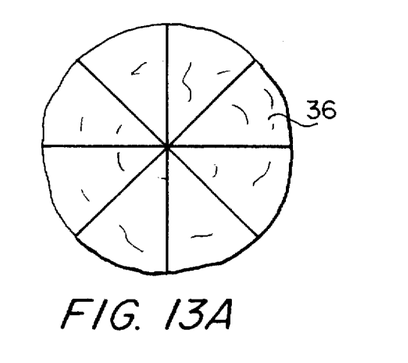
FIG. 13A is a transverse sectional view of tissue after it has been cut with four cutting filaments.

As FIG. 11 shows, the first top extractor ring 40 is moved upwardly. The cutting filament 38 connected to this extractor ring 40 is thus separated from its mounts to the wall of the bag 18 and to the base 32 of the bag 18 and cuts the tissue 36. Since the tissue 36 is held in place by the positioning pin 30 and the threaded casing 16, the tissue 36 cannot escape the cutting motion of the cutting filament 38. Due to the sequential extraction of the cutting filament 38 by means of the extractor rings 40, the tissue 36 is cut up into parts in the shape of orange sections, as shown in FIG. 13A. The cutting filaments 38 can have a rough, saw-like surface, in a favorable manner, to optimize the cutting process.

Figure 12:
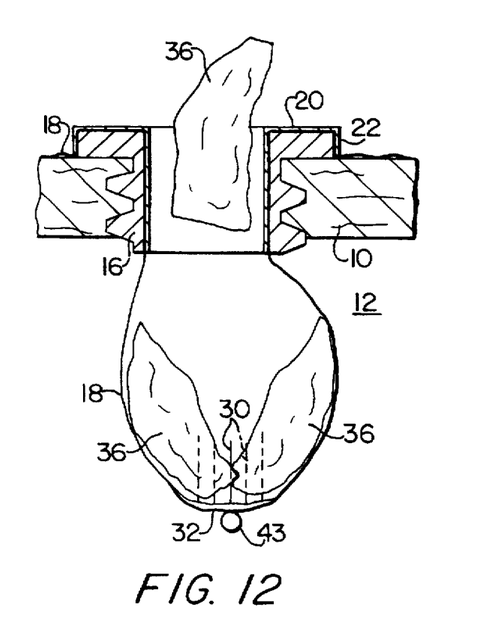
FIG. 12 is a side view schematic diagram depicting the removal of human tissue by use of the present invention.
Figure 14:
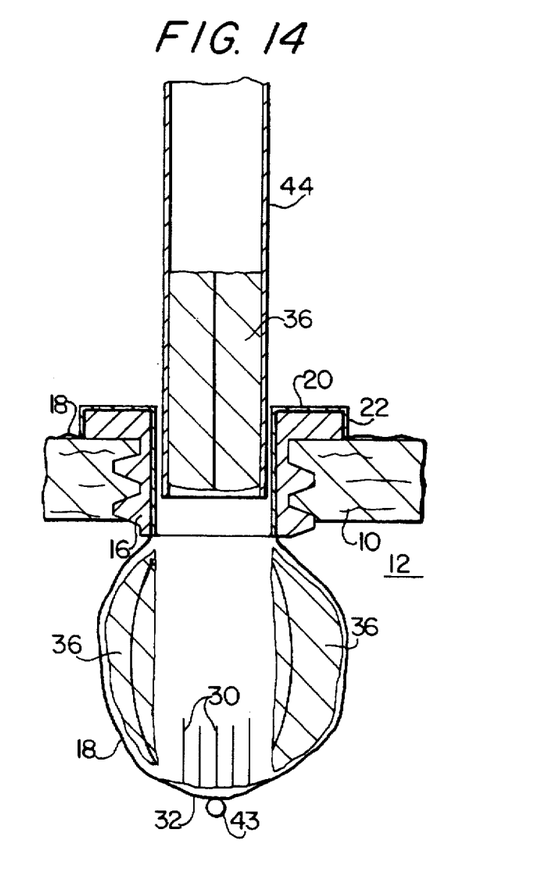
FIG. 14 is a partly sectional view showing the partial withdrawal of the hollow punch.
Figure 14A:
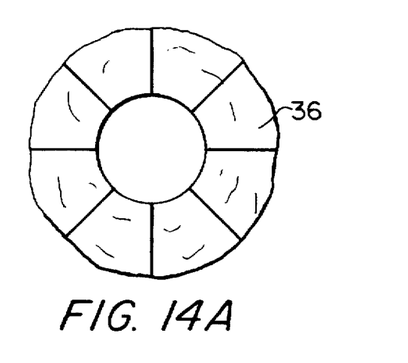
FIG. 14A shows the tissue after cutting by four filaments and removal of part thereof by the hollow punch.

After extracting all the cutting filaments 38, the tissue 36 has been cut into small pieces that can be removed through the threaded casing 16 and/or the insertion and safety casing 20, as FIG. 12 shows. The tissue pieces can also be punched out with the hollow cylinder punch 44 (FIG. 13). The volume from which the punched out tissue was removed (FIG. 14) is filled by the surrounding pieces of tissue, which are pressed together and migrate forward due to the compression action of the elastic bag 18 and the interior chamber of the abdomen. Due to repeated application of the cylinder punch 44, even large tumors can be easily and dependably removed. Once all pieces of the tissue 36 are removed the bag can be pulled out completely and the insertion and safety casing 20 and the threaded casing 16 are removed.

Although a number of embodiments of this invention have been mentioned by way of example, it is not intended that this invention be limited thereto. Accordingly, the invention should be considered to include any and all configurations, modifications, variations, combinations, equivalent arrangements or expansions falling within the scope of the following claims.

We claim:

1. A device for removal of tissue in a cavity in the human body including:
   a casing inserted in the abdominal wall surrounding the cavity,
   a flexible bag configured to be inserted through the casing, said bag comprising:
   (a) a first opening at a top portion of said bag, and positioned outwardly of said casing to thereby remain outside of said casing and said cavity when said bag is inserted through said casing into said cavity;

(b) a second opening in a side portion of said bag to receive tissue while said side portion is within said cavity after said bag is inserted through said casing into said cavity; and (c) a bottom portion providing a base of said bag opposite to said first opening, said bottom portion including an uptake volume arranged to hold tissue from said cavity when a portion of said bag, including said second opening, is withdrawn from said cavity through said casing;

said bag being collapsible from its bottom portion to said first opening to enable passage of said bag through said casing from adjacent said first opening to adjacent said bottom portion; and at least one cutting filament having (i) a center portion positioned inside and along said base of said bag, and (ii) two end portions positioned outside and above said first opening of said bag.

2. A device according to claim 1, further comprising an insertion and safety casing surrounding the part of said bag at said casino when said bag is inserted into said cavity through said first mentioned casing.

3. The device according to claim 2, further comprising a mandrin for engaging the base of the bag, and configured to introduce the bag through the casing into the cavity.

4. The device according to claim 3, wherein said at least one cutting filament is arranged with sawing filaments.

5. A device according to claim 4, wherein said cutting filaments are detachably mounted to an inner wall of said bag and to said base of said bag.

6. A device according to claim 5, further comprising mounting means for holding tissue in said bag, said mounting means being arranged within said bag.

7. A device according to claim 6, wherein said mounting means constituted by positioning pins is located at the base of said bag and directed inward to the interior of said bag.

8. A device according to claim 6, wherein said mounting means are constituted by a rough wall inside the surface of said bag.

9. A device according to claim 7, wherein said cutting filaments are arranged to pass through the positioning pins.

10. A device according to claim 1, wherein a plurality of cutting filaments are arranged in loops in the bottom portion of said bag.

11. A device according to claim 10, wherein one end of each of said cutting filaments is connected to an extractor ring for pulling said cutting filament out of said bag thereby passing through tissue contained in said bag.

12. A device according to claim 11, wherein a plurality of extractor rings are positioned vertically to enable them to be operated in sequence.

13. A device according to claim 1, further comprising a cylindrical punch having an inside wall arranged to pass through the first opening of the bag to reduce tissue contained in said bag.

14. A device according to claim 13, wherein said inside wall of said cylindrical punch includes a surface structure that does not permit sliding of the tissue within the cylindrical punch while the cylindrical punch is still within the cavity.

15. A device according to claim 13, wherein said cylindrical punch has a variable diameter.

16. The device according to claim 1, wherein said casing is threaded.

* * * * *

UNITED STATES PATENT AND TRADEMARK OFFICE
CERTIFICATE OF CORRECTION

PATENT NO. : 5,788,709
DATED      : August 4, 1998
INVENTOR(S): RIEK et al.

It is certified that error appears in the above-identified patent and that said Letters Patent is hereby corrected as shown below:

Claim 2, line 3, replace "casino" with --casing--.

Signed and Sealed this

Seventeenth Day of November, 1998

Attest:

BRUCE LEHMAN

*Attesting Officer*                *Commissioner of Patents and Trademarks*